(12) United States Patent
Herranen et al.

(10) Patent No.: US 9,018,189 B2
(45) Date of Patent: Apr. 28, 2015

(54) ANTI-INFLAMMATORY EFFECT OF MICROFIBRILLATED CELLULOSE

(75) Inventors: Kaisa Herranen, Pirkkala (FI); Mia Lohman, Otalampi (FI)

(73) Assignee: UPM-Kymmene Oyj Corporation, Helsinki (FI)

( * ) Notice: Subject to any disclaimer, the term of this patent is extended or adjusted under 35 U.S.C. 154(b) by 0 days.

(21) Appl. No.: 13/984,831

(22) PCT Filed: Feb. 10, 2012

(86) PCT No.: PCT/FI2012/050129
§ 371 (c)(1),
(2), (4) Date: Oct. 22, 2013

(87) PCT Pub. No.: WO2012/107648
PCT Pub. Date: Aug. 16, 2012

(65) Prior Publication Data
US 2014/0045785 A1    Feb. 13, 2014

(30) Foreign Application Priority Data
Feb. 11, 2011    (FI) ..................................... 20115135

(51) Int. Cl.
| | | |
|---|---|---|
| *A61K 31/717* | (2006.01) | |
| *A61K 8/73* | (2006.01) | |
| *A61L 15/28* | (2006.01) | |
| *A61P 17/00* | (2006.01) | |
| *A61P 17/02* | (2006.01) | |
| *A61P 17/06* | (2006.01) | |
| *A61K 31/715* | (2006.01) | |
| *A61L 15/44* | (2006.01) | |
| *A61Q 19/00* | (2006.01) | |
| *A61Q 5/00* | (2006.01) | |

(52) U.S. Cl.
CPC ............. *A61K 31/715* (2013.01); *A61K 31/717* (2013.01); *A61K 8/731* (2013.01); *A61L 15/28* (2013.01); *A61L 15/44* (2013.01); *A61L 2300/41* (2013.01); *A61Q 5/00* (2013.01); *A61Q 19/005* (2013.01)

(58) Field of Classification Search
None
See application file for complete search history.

(56) References Cited

U.S. PATENT DOCUMENTS

| | | | |
|---|---|---|---|
| 2007/0053960 A1 | 3/2007 | Brown | |
| 2010/0254961 A1 | 10/2010 | Nishio | |
| 2011/0053965 A1* | 3/2011 | Trigiante | ...................... 514/274 |

FOREIGN PATENT DOCUMENTS

| | | |
|---|---|---|
| EP | 0800267 A2 | 10/1997 |
| EP | 0726356 B1 | 4/2002 |
| FR | 2769836 A1 | 4/1999 |
| WO | 98/02486 A1 | 1/1998 |

OTHER PUBLICATIONS

Siro, I. et al "Microfibrillated cellulose and new nanocomposite materials . . . " Cellulose (2010) vol. 17, pp. 459-494.*
Groneberg, D. et al "Mast cells and vasculature in atopic dermatitis . . . " Allergy (2005) vol. 60, pp. 90-97.*
Trovatti, E. et al "Biocellulose membranes as supports . . . " Biomolecules (2011) vol. 12, pp. 4162-4168.*
Stoica-Guzun, A. et al "Effect of electron beam . . . " Nucl. Inst. Meth. Phys. Res. B (2007) vol. 265, pp. 434-438.*
International Search Report of PCT/FI2012/050129 (Jul. 26, 2012).
Finnish Search Report 20115135 (Oct. 28, 2011).

* cited by examiner

*Primary Examiner* — Leigh Maier
(74) *Attorney, Agent, or Firm* — Nixon Peabody LLP; Elizabeth W. Balo; Leena H. Karttunen Contarino

(57) ABSTRACT

The invention relates to use of microfibrillated cellulose as an anti-inflammatory agent for treatment of skin disorders.

14 Claims, 5 Drawing Sheets

| PCR array H-Atopic dermatitis 32 | | Stimulated control | NFκB inhibitor III 5 μm | | Microfibrillated cellulose 0.01% | |
|---|---|---|---|---|---|---|
| Gene name | abbrev | Cycles | Cycles | % control (Average HK) | Cycles | % control (Average HK) |
| Average Housekeeping | Avg HK | | | 100 | | 100 |
| Ribosomal protein L13a | RPL13A | 19,92 / 19,97 | 19,82 / 19,76 | 83 | 20,33 / 20,54 | 88 |
| Glyceraldehyde-3-phosphate dehydrogenase | GAPDH | 18,78 / 18,74 | 18,29 / 18,19 | 107 | 18,99 / 18,97 | 105 |
| *Antimicrobial peptide, innate immunity* | | | | | | |
| Toll-like receptor 3 | TLR3 | 27,08 / 26,64 | 27,88 / 27,91 | a) 36 | 26,86 / 26,82 | 123 |
| S100 calcium binding protein A7 | S100A7 | 26,72 / 26,64 | 32,68 / 32,22 | a) 1 | 25,47 / 25,64 | b) 268 |
| S100 calcium binding protein A11 | S100A11 | 19,14 / 19,50 | 19,54 / 19,67 | a) 61 | 19,52 / 19,64 | 102 |
| Ribonuclease, RNase A family, 7 | RNASE7 | 24,32 / 24,31 | 26,46 / 26,55 | a) 16 | 24,13 / 24,08 | 142 |
| Cathelicidin antimicrobial peptide | CAMP | 30,46 / 30,72 | 31,25 / 31,10 | a) 50 | 30,08 / 30,11 | b) 172 |
| *Interleukin family members* | | | | | | |
| Thymic stromal lymphopoietin | TSLP | 34,28 / 34,22 | 38,52 / 38,52 | a) 4 | 35,01 / 34,72 | 81 |
| Interleukin 1, alpha | IL1A | 19,81 / 19,82 | 20,61 / 21,01 | a) 38 | 19,58 / 19,78 | 135 |
| Interleukin 18 (interferon-gamma-inducing factor) | IL18 | 31,30 / 30,82 | 33,35 / 33,70 | a) 13 | 31,11 / 30,75 | 134 |
| Interferon, alpha 2 | IFNA2 | 36,41 / 36,49 | 35,68 / 35,70 | 127 | 34,54 / 33,94 | b) 580 |
| Interferon, beta 1, fibroblast | IFNB1 | 27,47 / 27,43 | 29,86 / 29,32 | a) 17 | 27,13 / 27,16 | b) 152 |
| Interleukin 4 receptor | IL4R | 32,77 / 33,20 | 35,80 / 35,50 | a) 12 | 33,71 / 33,51 | 79 |

Fig. 1

| PCR array H-Atopic dermatitis 32 | | Stimulated control | NFκB inhibitor III 5 µm | | Microfibrillated cellulose 0.01% | |
|---|---|---|---|---|---|---|
| Gene name | abbrev | Cycles | Cycles | % control (Average HK) | Cycles | % control (Average HK) |
| Chemokines | | | | | | |
| Interleukin 8 | IL8 | 24,01<br>24,60 | 27,47<br>27,11 | a) 9 | 25,32<br>25,21 | a) 62 |
| Chemokine (C-C motif) ligand 3 | CCL3 | 19,94<br>20,14 | 23,32<br>23,72 | a) 7 | 19,85<br>20,08 | 129 |
| Chemokine (C-C motif) ligand 5 | CCL5 | 17,23<br>17,00 | 17,30<br>17,40 | a) 63 | 17,07<br>17,19 | 121 |
| Chemokine (C-C motif) ligand 7 | CCL7 | 32,90<br>32,99 | 34,80<br>34,80 | a) 21 | 33,39<br>32,97 | 105 |
| Chemokine (C-C motif) ligand 13 | CCL13 | nd<br>nd | nd<br>nd | nd | nd<br>nd | nd |
| Chemokine (C-C motif) ligand 20 | CCL20 | 23,04<br>22,84 | 26,51<br>26,63 | a) 6 | 21,91<br>22,12 | b) 233 |
| Chemokine (C-C motif) ligand 17 | CCL17 | nd<br>nd | nd<br>nd | nd | nd<br>nd | nd |
| Chemokine (C-C motif) ligand 11 | CCL11 | nd<br>nd | nd<br>nd | nd | nd<br>nd | nd |
| Chemokine (C-C motif) ligand 22 | CCL22 | 28,51<br>28,66 | 26,21<br>26,00 | b) 418 | 28,17<br>28,16 | b) 164 |
| Chemokine (C-C motif) ligand 27 | CCL27 | 24,81<br>24,91 | 28,31<br>28,09 | a) 7 | 24,65<br>24,72 | 139 |
| Differentiation markers | | | | | | |
| Involucrin | IVL | 30,07<br>30,09 | 31,76<br>31,22 | a) 29 | 29,26<br>28,84 | b) 253 |
| Filaggrin | FLG | 31,45<br>32,04 | 31,72<br>32,10 | 66 | 30,32<br>29,87 | b) 382 |
| Loricrin | LOR | 34,34<br>34,51 | 33,98<br>34,09 | 98 | 33,47<br>33,47 | b) 238 |
| Keratin 10 | KRT10 | 33,12<br>33,03 | 31,57<br>31,10 | b) 253 | 32,23<br>32,43 | b) 206 |
| LAG1 homolog, ceramide synthase 6 | LASS6 | 29,57<br>29,27 | 29,06<br>28,84 | 103 | 28,87<br>28,64 | b) 194 |
| Cell-cell interactions | | | | | | |
| Corneodesmosin | CDSN | 24,21<br>24,12 | 27,46<br>27,30 | a) 8 | 24,35<br>24,02 | 122 |
| Transcriptional regulation | | | | | | |
| Retinoic acid receptor responder (tazarotene induced) 3 | RARRES3 | 24,30<br>24,08 | 25,32<br>24,93 | a) 39 | 24,25<br>24,51 | 108 |
| B-cell CLL/lymphoma 3 | BCL3 | 29,72<br>29,28 | 28,78<br>28,70 | 125 | 28,62<br>28,94 | b) 201 |
| Oxidative and cellular stress response | | | | | | |
| Heme oxygenase (decycling) 1 | HMOX1 | 27,09<br>27,58 | 29,30<br>29,34 | a) 19 | 26,58<br>26,83 | b) 188 |

Fig. 1 (continued)

| PCR array H-Keratinocyte 64 | | Control | CaCl₂ at 1.5 mM | | Microfibrillated | |
|---|---|---|---|---|---|---|
| Gene name | abbrev | Cycles | Cycles | % control (Average HK) | Cycles | % control (Average HK) |
| Average Housekeeping | Avg HK | | | 100 | | 100 |
| Ribosomal protein L13a | RPL13A | 19,22 / 19,26 | 18,57 / 18,62 | 110 | 19,64 / 19,66 | 75 |
| Actin, beta | ACTB | 18,08 / 18,21 | 17,59 / 17,63 | 102 | 18,36 / 18,17 | 91 |
| Glyceraldehyde-3-phosphate dehydrogenase | GAPDH | 18,22 / 18,21 | 17,86 / 17,74 | 94 | 18,54 / 18,56 | 79 |
| Differentiation markers | | | | | | |
| Calmodulin-like 5 | CALML5 | 33,67 / 33,91 | 30,84 / 30,83 | b) 542 | 33,62 / 33,43 | 119 |
| Cornulin | CRNN | 33,32 / 33,41 | 33,48 / 33,71 | a) 60 | 33,63 / 33,75 | 79 |
| Filaggrin | FLG | 29,04 / 28,86 | 26,56 / 27,02 | b) 317 | 28,99 / 28,75 | 105 |
| Involucrin | IVL | 28,35 / 28,61 | 25,53 / 25,57 | b) 532 | 28,34 / 28,28 | 111 |
| Keratin 1 | KRT1 | 29,77 / 29,87 | 27,47 / 27,49 | b) 355 | 29,87 / 29,76 | 100 |
| Keratin 10 | KRT10 | 31,56 / 31,84 | 30,97 / 30,66 | 130 | 31,95 / 31,84 | 86 |
| Keratin 2 | KRT2 | 34,57 / 34,20 | 33,67 / 33,68 | 114 | 34,41 / 34,01 | 112 |
| Keratin 6A NM_005554 | KRT6A | 20,78 / 20,79 | 19,55 / 19,21 | b) 187 | 21,03 / 21,57 | 71 |
| Loricrin | LOR | 34,96 / 35,69 | 34,46 / 35,57 | 91 | 34,32 / 34,63 | b) 174 |
| Peptidyl arginine deiminase, type I | PADI1 | 33,63 / 33,61 | 29,75 / 30,11 | b) 912 | 33,50 / 32,60 | b) 154 |
| Small proline-rich protein 1A | SPRR1A | 23,87 / 23,82 | 19,89 / 20,09 | b) 1017 | 24,06 / 23,91 | 90 |
| Small proline-rich protein 1B (cornifin) | SPRR1B | 22,52 / 22,13 | 18,78 / 18,81 | b) 803 | 22,22 / 22,14 | 109 |
| Small proline-rich protein 2A | SPRR2A | 31,82 / 31,93 | 26,89 / 26,80 | b) 2291 | 31,78 / 31,81 | 105 |
| Transglutaminase 1 (K polypeptide epidermal type I, protein-glutamine-gamma-glutamyltransferase) | TGM1 | 24,52 / 24,25 | 20,36 / 20,29 | b) 1165 | 24,46 / 24,48 | 93 |
| Lipide synthesis | | | | | | |
| Acyl-CoA synthetase short-chain family member 2 | ACSS2 | 23,25 / 23,27 | 22,66 / 22,63 | 107 | 23,58 / 23,07 | 96 |
| Fatty acid binding protein 5 (psoriasis-associated) | FABP5 | 24,18 / 24,17 | 23,29 / 23,27 | 130 | 24,60 / 24,64 | 73 |
| Fatty acid synthase | FASN | 25,27 / 25,48 | 24,81 / 24,89 | 101 | 25,51 / 25,46 | 92 |
| Glucosidase, beta; acid (includes glucosylceramidase) | GBA | 25,24 / 25,15 | 24,31 / 24,38 | 126 | 25,58 / 25,62 | 75 |
| Sphingomyelin phosphodiesterase 1, acid lysosomal | SMPD1 | 32,96 / 33,28 | 33,27 / 33,09 | 67 | 34,34 / 33,94 | a) 49 |
| Serine palmitoyltransferase, long chain base subunit 1 | SPTLC1 | 23,68 / 23,72 | 23,02 / 23,04 | 112 | 24,07 / 24,11 | 76 |
| Sulfotransferase family, cytosolic, 2B, member 1 | SULT2B1 | 27,91 / 27,93 | 23,47 / 23,74 | b) 1402 | 27,96 / 27,80 | 102 |
| UDP-glucose ceramide glucosyltransferase | UGCG | 25,00 / 24,71 | 23,76 / 23,69 | b) 153 | 25,11 / 25,47 | 74 |

Fig. 2

| PCR array H-Keratinocyte 64 | | Control | CaCl₂ at 1.5 mM | | Microfibrillated | |
|---|---|---|---|---|---|---|
| Gene name | abbrev | Cycles | Cycles | % control (Average HK) | Cycles | % control (Average HK) |
| Proliferation marker | | | | | | |
| Keratin 19 | KRT19 | 25,96<br>26,07 | 23,63<br>23,65 | b) 364 | 26,09<br>26,11 | 93 |
| Desquamation | | | | | | |
| Kallikrein-related peptidase 5 | KLK5 | 23,21<br>23,06 | 21,17<br>21,34 | b) 258 | 22,84<br>22,95 | 117 |
| Kallikrein-related peptidase 7 | KLK7 | 24,37<br>24,30 | 20,30<br>20,27 | b) 1162 | 24,71<br>24,74 | 76 |
| Dermo-epidermal junction | | | | | | |
| Collagen, type IV, alpha 1 | COL4A1 | 26,34<br>26,45 | 26,48<br>26,54 | a) 65 | 26,67<br>26,71 | 81 |
| Collagen, type VII, alpha 1 | COL7A1 | 25,52<br>25,52 | 25,94<br>26,03 | a) 51 | 25,47<br>25,53 | 101 |
| Laminin, gamma 2 | LAMC2 | 22,87<br>22,76 | 22,34<br>22,67 | 87 | 22,66<br>22,77 | 106 |
| Growth factors / Mitotic factors | | | | | | |
| Epidermal growth factor (beta-urogastrone) | EGF | 34,75<br>34,51 | 33,69<br>33,95 | 123 | 34,91<br>34,34 | 101 |
| Epidermal growth factor receptor (erythroblastic leukemia viral (v-erb-b) oncogene homolog, avian) | EGFR | 22,30<br>22,30 | 22,37<br>22,35 | 67 | 22,68<br>22,58 | 79 |
| Hyaluronan synthase 3 | HAS3 | 31,21<br>30,66 | 31,44<br>31,00 | a) 57 | 30,85<br>30,67 | 110 |
| Heparin-binding EGF-like growth factor | HBEGF | 25,92<br>26,03 | 26,01<br>26,00 | 69 | 26,36<br>26,25 | 79 |
| Transforming growth factor, beta 1 | TGFB1 | 26,64<br>26,54 | 26,47<br>26,36 | 79 | 26,44<br>26,88 | 96 |
| Water, glycerol transport | | | | | | |
| Aquaporin 3 (Gill blood group) | AQP3 | 22,77<br>22,93 | 21,49<br>21,48 | b) 180 | 22,93<br>23,13 | 88 |
| Apoptosis | | | | | | |
| Caspase 14, apoptosis-related cysteine peptidase | CASP14 | 27,75<br>27,94 | 26,69<br>26,81 | 150 | 27,85<br>27,79 | 101 |
| Inflammation | | | | | | |
| Chemokine (C-X-C motif) ligand 5 | CXCL5 | 32,05<br>32,23 | 31,77<br>31,92 | 86 | 32,66<br>33,08 | a) 60 |
| Interleukin 1, alpha | IL1A | 22,84<br>22,75 | 22,17<br>22,31 | 103 | 23,08<br>22,91 | 86 |
| Interleukin 1 receptor antagonist | IL1RN | 23,04<br>23,05 | 20,79<br>20,81 | b) 333 | 23,44<br>23,34 | 78 |
| Interleukin 8 | IL8 | nd<br>nd | nd<br>nd | nd | nd<br>nd | nd |

Fig. 2 (continued)

| PCR array H-Keratinocyte 64 | | Control | CaCl$_2$ at 1.5 mM | | Microfibrillated | |
|---|---|---|---|---|---|---|
| Gene name | abbrev | Cycles | Cycles | % control (Average HK) | Cycles | % control (Average HK) |
| Antimicrobial peptide, innate immunity | | | | | | |
| Cathelicidin antimicrobial peptide | CAMP | 30,76 / 30,84 | 30,82 / 30,88 | 68 | 30,26 / 30,66 | 127 |
| Defensin, beta 4 | DEFB4 | 34,21 / 33,92 | 32,15 / 31,78 | b) 302 | 33,12 / 33,74 | b) 157 |
| Peptidase inhibitor 3, skin-derived | PI3 | 26,61 / 26,69 | 22,59 / 22,63 | b) 1154 | 25,97 / 26,58 | 131 |
| Ribonuclease, RNase A family, 7 | RNASE7 | 25,67 / 25,71 | 25,53 / 25,63 | 76 | 26,48 / 26,45 | a) 58 |
| S100 calcium binding protein A7 | S100A7 | 31,58 / 31,73 | 29,08 / 29,52 | b) 363 | 32,07 / 32,89 | a) 58 |
| cell-cell interactions, epidermal cohesion | | | | | | |
| Corneodesmosin | CDSN | 29,79 / 30,26 | 26,47 / 26,54 | b) 794 | 30,63 / 30,48 | 68 |
| Claudin 1 | CLDN1 | 21,91 / 21,92 | 20,68 / 20,77 | b) 160 | 21,90 / 22,04 | 96 |
| Catenin (cadherin-associated protein), alpha 1, 102kDa | CTNNA1 | 26,05 / 26,16 | 25,29 / 25,62 | 111 | 25,97 / 26,01 | 107 |
| Desmoglein 1 | DSG1 | 29,79 / 29,87 | 26,95 / 26,89 | b) 527 | 29,87 / 30,06 | 90 |
| Desmoplakin | DSP | 20,37 / 20,47 | 19,20 / 19,27 | b) 159 | 20,83 / 20,71 | 78 |
| Epiplakin 1 | EPPK1 | 30,33 / 29,84 | 30,51 / 30,63 | a) 49 | 31,09 / 31,33 | a) 45 |
| Envoplakin | EVPL | 29,18 / 28,92 | 29,29 / 29,05 | a) 65 | 30,28 / 30,17 | a) 44 |
| Integrin, alpha 2 (CD49B, alpha 2 subunit of VLA-2 receptor) | ITGA2 | 25,79 / 25,67 | 25,11 / 25,05 | 110 | 26,15 / 26,12 | 75 |
| Secreted protein, acidic, cysteine-rich (osteonectin) | SPARC | 21,71 / 21,80 | 21,80 / 21,69 | 71 | 22,13 / 22,15 | 76 |
| Dystonin | DST | 20,21 / 20,40 | 21,01 / 21,17 | a) 41 | 20,90 / 20,90 | 66 |
| CD44 molecule (Indian blood group) | CD44 | 22,66 / 22,60 | 22,20 / 22,07 | 99 | 22,93 / 22,77 | 85 |
| Syndecan 1 | SDC1 | 21,79 / 21,68 | 20,48 / 20,51 | b) 166 | 21,80 / 21,80 | 95 |
| Extracellular matrix degradation, regeneration-related markers | | | | | | |
| Matrix metallopeptidase 3 (stromelysin 1, progelatinase) | MMP3 | 31,87 / 31,89 | 33,87 / 33,97 | a) 17 | 32,03 / 32,61 | 75 |
| Matrix metallopeptidase 9 (gelatinase B, 92kDa gelatinase, 92kDa type IV collagenase) | MMP9 | 27,94 / 28,15 | 27,48 / 27,30 | 110 | 28,34 / 28,19 | 85 |
| Stratifin | SFN | 21,68 / 21,34 | 21,33 / 21,02 | 88 | 21,92 / 21,97 | 73 |
| Oxidative and cellular stress response | | | | | | |
| Heme oxygenase (decycling) 1 | HMOX1 | 30,45 / 30,43 | 28,70 / 28,86 | b) 222 | 30,09 / 30,44 | 113 |
| Heat shock 27kDa protein 1 | HSPB1 | 21,29 / 21,28 | 21,16 / 21,27 | 74 | 22,00 / 21,97 | a) 61 |

Fig. 2 (continued)

ANTI-INFLAMMATORY EFFECT OF MICROFIBRILLATED CELLULOSE

CLAIM OF PRIORITY

This application claims priority under 35 USC 371 to International Application No. PCT/FI2012/050129, filed on Feb. 10, 2012, which claims priority to Finland Application Serial No. 20115135, filed Feb. 11, 2011, each of which is incorporated by reference in its entirety.

FIELD OF THE INVENTION

The present invention relates to the external use of a microfibrillated cellulose, particularly for the care and treatment of skin.

BACKGROUND OF THE INVENTION

Cellulose is an organic compound, polysaccharide, consisting of a linear chain of several D-glucose units linked through β(1,4) glycosidic bonds. Many properties of cellulose depend on its chain length or degree of polymerization, the number of glucose units that make up one polymer molecule. Cellulose is mainly obtained from wood pulp and cotton but may be also secreted by some species of bacteria to form biofilms.

Microfibrillated cellulose (MFC) or nanocellulose is a material composed of cellulose fibrils, i.e. basic structural components of wood with a high length to diameter ratio (aspect ratio). The microfibrillated cellulose can be prepared from any cellulose containing material including wood (pulp fibres).

Generally, the cellulose fibrils are used in cosmetic compositions e.g. as a composite coating agent for hair, eyelashes or nails. Microfibrils are used, for example to improve the lengthening of the eyelashes. Microfibrillated cellulose may also be used as a binder or filler for solid dosage forms and as a bodying agent or a drug carrier in topical formulations or dermatological products. Additionally, cellulose fibrils may be used as a stabilizer for surfactant free oil-in-water emulsions.

European patent EP 820267 and the corresponding U.S. Pat. No. 6,001,338 disclose the use of an aqueous solution or dispersion of a film-forming polymer and an aqueous suspension of natural cellulose microfibrils as a composite coating agent for hair, eyelashes, eyebrows and nails. The aim is to use cellulose microfibrils in cosmetics to improve the physical properties of cosmetic compositions.

Publication US 2002/192251 deals with cosmetic compositions, especially mascara, intended for human keratinous substances such as the skin, nails or keratinous fibers (eyelashes, eyebrows and hair) and containing a mixture of cellulose nanofibrils or microfibrils with second fiber and wax.

Up to now, in connection with human body, microfibrillated cellulose has only been proposed for enhancing properties of cosmetic formulations.

The skin is made up of layers of epidermis, dermis and subcutis. The epidermis is the outer layer of the skin and consists of sublayers: stratum corneum, granulosum, spinosum and basal layer. Keratinocytes are the main type of cells which make up the epidermis. The dermis is the middle layer of the skin and is held together by collagen made by fibroblasts. The subcutis or a subcutaneous layer is the deepest layer of the skin and consists of a network of collagen and fat cells.

There are a number of causes for skin inflammation (dermatitis), e.g. irritants such as some chemicals, overexposure to sun; infections; chronic or acute inflammatory conditions.

There are chronic and inflammatory skin conditions and disorders like atopic dermatitis, a type of eczema, for which there is currently no cure available. For controlling the symptoms, various treatments may be used, such as topical treatments focusing on reducing both dryness and inflammation of the skin, e.g. moisturizers. However, the moisturizers should not have any ingredients that may further irritate or aggravate the skin condition. Also topical corticosteroid products may be used. However, using steroids involves disadvantages, such as thinning of the skin. High potency steroids should also be avoided on the face or other areas where the skin is naturally thin. If there are also infections involved, antibiotics may be employed.

There remains a need for improved and efficient products comprising dermatological compositions with an anti-inflammation activity which allow local treatment of different chronic skin disorders, such as atopic dermatitis and psoriasis, while at same time avoiding the side effects and disadvantages of conventional treatments.

SUMMARY OF THE INVENTION

It is an object to provide a use of a natural based ingredient, which has an anti-inflammatory effect, for topical care and/or treatment of skin inflammation conditions and disorders.

According to a first aspect of the present invention there is provided microfibrillated cellulose for use as an anti-inflammatory agent for the treatment of skin inflammation. Also a method of use of microfibrillated cellulose as an anti-inflammatory agent for the treatment of skin inflammation is provided.

According to a second aspect of the present invention there is provided microfibrillated cellulose for use in preventing inflammation induced keratinocyte de-differentiation. Also a method of use of microfibrillated cellulose in preventing inflammation induced keratinocyte de-differentiation is provided.

According to a third aspect of the present invention there is provided microfibrillated cellulose for use in the treatment of atopic dermatitis. Also a method of use of microfibrillated cellulose in the treatment of atopic dermatitis is provided.

According to a fourth aspect of the present invention there is provided microfibrillated cellulose for use in the treatment of psoriasis. Also a method of use of microfibrillated cellulose in the treatment of psoriasis is provided.

According to a fifth aspect of the present invention there is provided microfibrillated cellulose for use in the treatment of skin burns. Also a method of use of microfibrillated cellulose in the treatment of skin burns is provided.

Further embodiments of the invention are presented in the dependent claims.

The microfibrillated cellulose is included in an ointment, a serum, an aqueous gel, a foam, a cream, an emulsion of aqueous and fatty phase, a lotion, or a paste.

DESCRIPTION OF THE DRAWINGS

In the following, the invention will be discussed with reference to accompanying figures, in which FIG. 1 shows test results of anti-inflammatory effects of microfibrillated cellulose on the gene expression profile of normal human epidermal keratinocytes, FIG. 2 shows test results of the effects of microfibrillated cellulose on skin moisture and barrier function on the gene expression profile of normal human epidermal keratinocytes.

DETAILED DESCRIPTION OF THE INVENTION

According to the present invention there is provided a method of use and use of a natural based ingredient for the treatment of keratinous material providing beneficial skin effects such as an activity against skin inflammation conditions. The ingredient may be multifunctional and provide also other beneficial effects.

According to the invention the natural based ingredient is microfibrillated cellulose (MFC). There are several widely used synonyms for microfibrillated cellulose. For example: nanofibrillated cellulose, nanocellulose, microfibrillar cellulose, nanofibrillar cellulose, cellulose nanofiber, nano-scale fibrillated cellulose, or cellulose microfibrils. Microfibrillated cellulose described in this application is not the same material as the so-called cellulose whiskers, which are also known as: cellulose nanowhiskers, cellulose nanocrystals, cellulose nanorods, rod-like cellulose microcrystals or cellulose nanowires. In some cases, similar terminology is used for both materials, for example by Kuthcarlapati et al. (Metals Materials and Processes 20(3):307-314, 2008) where the material investigated was called "cellulose nanofibers" although cellulose nanowhiskers were clearly referred to. Typically these materials do not have amorphous segments along the fibrillar structure as microfibrillar cellulose, which leads to a more rigid structure.

According to the invention, microfibrillated cellulose, MFC, is used as an anti-inflammatory agent for the treatment of skin disorders, such as skin inflammation conditions. When the MFC is used as anti-inflammatory agent, it provides anti-inflammatory effects, i.e. calming and soothing effects, but it may also participate in other useful actions such as skin moisturizing. It may also be used for treatments of acute disorders to facilitate the symptoms of irritated skin and/or participate in or promote a healing process of the skin. The MFC may be used for example to help manage discomfort such as itching and rash of sun burns.

The microfibrillated cellulose, MFC, may be used as an active agent and/or as an ingredient in cosmetic and/or dermatological products. These products are preferably used for external and topical application onto keratinous materials such as the skin, the scalp, the lips and the eyelids.

The cosmetic and/or dermatological product is preferably semi-solid at room temperature and is easily absorbed into the outer layer of the skin, i.e. the stratum corneum.

The product comprising MFC may be in all the usual forms suitable for dermatological or cosmetic indication and for administration such as topical application, for example in the form of an ointment, a serum, an aqueous gel, a foam, a cream, an emulsion of aqueous and fatty phase, a lotion, or a paste. Additionally, MFC may be included in wound healing products, such as films, membranes or fabrics.

If necessary, the cosmetic or dermatological product may further include various components or ingredients which are compatible with the skin. The ingredients may be chosen according to the form of administration selected and may contain, but are not limited to, excipients and carriers such as gelling agents, stabilizers, surfactants, emulsifiers, thickeners, vitamins, oils, humectants, ultraviolet absorbers, preservatives, water, alcohol, colouring materials.

According to the invention MFC acts as an anti-inflammatory agent for the treatment of skin inflammation. The concentrations of micro fibrils (an active principle or dry matter of MFC), acting as an anti-inflammatory agent when incorporated in the product for the treatment of skin, may range from 0.00010% to 1.3% or even 4%.

MFC may have different physical forms. It may be in the form of an aqueous dispersion, a film-like structure such as wet or dry membrane, non-woven or woven fabric.

In addition to its anti-inflammatory property, MFC may also provide a pleasant texture and act as a bodying agent (thickener) for the product. The thickener provides a suitable viscosity for the product. The suitable viscosity is important allowing the product to remain in place upon application to the skin. If necessary, the product may also include other thickeners in addition to MFC. MFC may also act as a stabilizer. It may also be used for emulsification of the product.

According to the invention, the cellulose microfibrils are extracted from a cellulose raw material source such as wood. The wood material can be obtained from softwood trees, such as spruce, pine, fir, larch, douglas-fir or hemlock, or from hardwood trees, such as birch, aspen, poplar, alder, eucalyptus or acacia, or from a mixture of softwoods and hardwoods. Alternatively, the micro fibrils may originate from a non-wood material such as cotton or bacteria. The non-wood material can be obtained from agricultural residues, grasses or other plant substances such as straw, leaves, bark, seeds, hulls, flowers, vegetables or fruits from cotton, corn, wheat, oat, rye, barley, rice, flax, hemp, manila hemp, sisal hemp, jute, ramie, kenaf, bagasse, bamboo or reed.

The term "microfibrillated cellulose, (MFC)" refers to a collection of isolated cellulose microfibrils or microfibril bundles derived from cellulose raw material. The cellulose fibrils may be isolated from wood based fibres through high-pressure, high temperature and high velocity impact homogenization. The homogenization process is used to delaminate or disintegrate the cell walls of the fibres and to liberate their sub-structural fibrils and micro fibrils. Enzymatic and/or mechanical pre-treatments of wood fibres may also be used. MFC is in native form, which has not undergone any chemical modification. The invention also encompasses chemical modifications of the native cellulose.

Cellulose microfibrils typically have a high aspect ratio: the length might exceed one micrometer while the number-average diameter is typically below 200 nm. The diameter of micro fibril bundles can also be larger but is generally less than 1 μm. The smallest micro fibrils are similar to the so called elementary fibrils, which are typically 2-20 nm in diameter. However, the present invention is not intended to be limited to these values. The dimensions of the fibrils or fibril bundles are dependent on the raw material and the disintegration method. The micro fibrillated cellulose may also contain some hemicelluloses; the amount may be dependent on the plant source.

The MFC is not cytotoxic to fibroblasts or to keratinocytes i.e. it does not cause mortality of the cells.

According to the invention, the MFC has an anti-inflammatory effect. The MFC has been found to efficiently reduce the inflammation of the skin. The microfibrillated cellulose limits the side-effects of inflammation in keratinocytes by preventing inflammation-induced keratinocyte dedifferentiation, for example in the case of an atopic dermatitis skin condition. MFC may also be effective for the treatment of other skin inflammation conditions such as psoriasis and skin burns. Skin burns may be a type of injury to flesh and may be caused e.g. by heat, chemicals, light, radiation, or friction.

EXAMPLES

The following examples serve to illustrate the invention, without, however, being limiting in nature.

Example 1

Microfibrillated cellulose (MFC) was evaluated for its effects on skin using different skin biology-related in vitro models. The skin anti-inflammatory effects and moisture and barrier function were evaluated. For in vitro tests in normal human epidermal keratinocytes (NHEK), the test concentration of MFC was 0.01% (0.00016% active principle). Cell type of normal human epidermal keratinocytes (NHEK) in culture conditions of 37° C., 5% $CO_2$ was used. Culture medium of NHEK consists of keratinosyte-serum free medium (SFM) supplemented with epidermal growth factor (EGF) 0.25 ng/ml, pituitary extract (PE) 25 µg/ml and gentamycin 25 µg/ml. The test and the results are described in more detail in Examples 1.1-1.2.

Example 1.1

NHEK Inflammation

The anti-inflammatory effects of the MFC compound (i.e. soothing, calming properties) were evaluated on the gene expression profile of normal human epidermal keratinocytes (NEHK) stimulated with an association of poly(I:C) and inflammatory cytokines. Inflammatory cytokines are natural small protein molecules involved in a variety of immunological and inflammatory phenomen. Effects of the compound were evaluated on gene expression profile using RT-qPCR technology on mRNA extracted from cell layers. Extracted mRNAs were analyzed on a dedicated PCR array containing 32 target genes, including 2 housekeeping genes, selected for their importance in skin inflammation and their involvement in atopic dermatitis disease.

Keratinocytes were seeded in a culture medium and cultured for 24 hours. The medium was then replaced by an assay medium. The assay medium consisted of a keratinocyte-serum free medium (SFM) supplemented with gentamycin 25 µg/ml. After an adaptation time, the medium was replaced by assay medium containing or not (in the case of control) the test compound of MFC or the reference of NFκB inhibitor III at 5 µM, and the cells were pre-incubated for 24 hours. The assay medium was then renewed and the cells were treated identically treated with test compound or the references in the presence or not (in the case of non-stimulated control) of the association of Poly(I:C) and the Th2 type cytokine mix and the cells were incubated for 24 hours. Three parallel experiments were performed.

At the end of the incubation, supernatants were discarded and the cell layers were washed using phosphate buffered saline (PBS), and covered with TRI-Reagent®. The plates were immediately frozen at −80° C.

The test results are provided in FIG. 1. Atypical melting curves are indicated by the abbreviation nd. Down-regulated genes (arbitrary selection for inhibition: less than 65) are indicated by a), and up-regulated genes (arbitrary selection for stimulation: % more than 150) are indicated by b).

Treatment of NEHK with the association of poly(I:C) and cytokines clearly induced an inflammatory profile and induced a characteristic gene expression modulation of many markers involved in atopic dermatitis pathology. The treatment induced a strong up-regulation of all inflammatory markers analyzed in this PCR array, which was observed as the simultaneous increase of cytokine markers (IL1A, IL18, IFNB1, IL4R, TSLP), chemokine markers (CCL3, CCL5, CCL7, CCL20, CCL22, CCL27 and IL8) and innate immunity markers (TLR3, S100A7, S100A11, RNASE7). Inflammation of NHEK also resulted in a decreased expression of keratinocyte differentiation markers (FLG, IVL, KRT10, LASS6). The reference NFκB inhibitor III (5 µM) strongly inhibited the inflammation induced by the association of poly (I:C) and cytokines. Except for the keratinocyte differentiation markers, almost all the effects of pro-inflammatory association (increased expression of cytokine markers, chemokine markers and innate immunity markers) were reversed by the reference. These results were expected and validated the assay.

The main effects which can be expected from the test compound of MFC in this model will be [1] an anti-inflammatory effect: decreased expression of cytokine; chemokine and innate immunity related markers, and [2] a pro-differentiating effect. The pro-differentiating effect is expected since the inflammation induced in this model also results in keratinocyte dedifferentiation, which can be seen as a side-effect and which will in in vivo models affect skin's aspect and quality.

Based on the results shown in FIG. 1, the compound of micro fibrillated cellulose (MFC) was observed to reverse the effects of inflammation on keratinocyte differentiation even though it does not decrease the expression of inflammatory markers. All the differentiation markers analyzed (IVL, FLG, LOR, KRT10, LASS6) were observed to increase in the presence of MFC. Expression of several inflammatory markers, such as S100A7, CAMP, IFNA2, AFNB1, CCL20 and CCL22, were also found to increase. Expression of oxidative-stress related marker HMOX1 was also found to increase due to the presence of MFC.

MFC was shown as a compound limiting keratinocyte dedifferentiation in an inflammatory model mainly relevant for atopic dermatitis.

Based on the results it is found that MFC can be used to treat atopic dermatitis. In addition, it may be used for the treatment of other forms of skin inflammation e.g. psoriasis, skin burn etc.

Example 1.2

NHEK Differentiation

The effects on skin moisture and barrier function the compound of MFC was evaluated on the gene expression profile of normal human epidermal keratinocytes (NEHK) in basal conditions. Effects of the compound on keratinocytes were evaluated using RT-qPCR technology on mRNA extracted from cell layers. Extracted mRNAs were analyzed on a dedicated PCR array containing 64 target genes, including 3 housekeeping genes, selected for their importance in keratinocyte differentiation, growth and epidermal renewal.

Keratinocytes were seeded in culture medium and cultured for 48 hours. The medium was then replaced by an assay medium. The assay medium consisted of keratinocyte-serum free medium (SFM) supplemented with gentamycin 25 µg/ml. After an adaptation time, the medium was replaced by assay medium containing or not (in the case of control) the test compound or the reference of calcium chloride at 1.5 mM and the cells were incubated for 24 hours. Three parallel experiments were performed.

At the end of the incubation, supernatants were discarded and the cell layers were washed using phosphate buffered saline (PBS), and covered with TRI-Reagent®. The plates were immediately frozen at −80° C.

The test results are provided in FIG. 2. Atypical melting curves are indicated by the abbreviation nd. Down-regulated genes (arbitrary selection for inhibition: less than 65) are indicated by a), and up-regulated genes (arbitrary selection for stimulation: % more than 150) are indicated by b).

Based on the test results, MFC presented no pro-differentiating effect in basal conditions.

The invention claimed is:

1. A method of treatment of skin inflammation comprising topically administering to a subject affected with a condition or disease causing skin inflammation, a composition comprising plant-derived microfibrillated cellulose as an anti-inflammatory agent.

2. The method of treatment claim 1, wherein the plant-derived microfibrillated cellulose is included in an ointment, a serum, an aqueous gel, a foam, a cream, an emulsion of aqueous and fatty phase, a lotion, or a paste.

3. A method for preventing inflammation induced keratinocyte de-differentiation comprising topically administering plant-derived microfibrillated cellulose as an anti-inflammatory agent to a subject.

4. The method of claim 3, wherein the plant-derived microfibrillated cellulose is included in an ointment, a serum, an aqueous gel, a foam, a cream, an emulsion of aqueous and fatty phase, a lotion, or a paste.

5. The method of claim 1 wherein the skin inflammation causing condition or disease is atopic dermatitis.

6. The method of claim 5, wherein the plant-derived microfibrillated cellulose is included in an ointment, a serum, an aqueous gel, a foam, a cream, an emulsion of aqueous and fatty phase, a lotion, or a paste.

7. The method of claim 1, wherein the skin inflammation causing condition or disease is psoriasis.

8. The method of claim 7, wherein the plant-derived microfibrillated cellulose is included in an ointment, a serum, an aqueous gel, a foam, a cream, an emulsion of aqueous and fatty phase, a lotion, or a paste.

9. The method of claim 1, wherein the plant-derived microfibrillated cellulose is formulated into a film, a membrane or a woven or non-woven fabric.

10. The method of claim 1, wherein the concentration of microfibrillated cellulose in the composition is 0.00010% to 4%.

11. The method of claim 10, wherein the concentration of the microfibrillated cellulose in the composition is 0.00010% to 1.3%.

12. The method of claim 1, wherein the plant-derived microfibrillated cellulose is derived from wood-based fibers.

13. The method of claim 12, wherein the wood-based fibers are derived from softwood trees or hardwood trees.

14. The method of claim 1, wherein the plant-derived microfibrillated cellulose is derived from cotton, agricultural residue, grass, straw, leaves, bark, seeds, hulls, flowers, vegetables or fruits from cotton, corn, wheat, oat, rye, barley, rice, flax, hemp, manila hemp, sisal hemp, jute, ramie, kenaf, bagasse, bamboo or reed.

\* \* \* \* \*